United States Patent [19]

Brenner et al.

[11] Patent Number: 5,340,452
[45] Date of Patent: Aug. 23, 1994

[54] ON-COLUMN PRECONCENTRATION OF SAMPLES IN CAPILLARY ELECTROPHORESIS

[75] Inventors: Nathaniel Brenner, Irvine; Richard H. Palmieri, Cupertino, both of Calif.

[73] Assignee: Beckman Instruments, Inc., Fullerton, Calif.

[21] Appl. No.: 649,385

[22] Filed: Feb. 1, 1991

[51] Int. Cl.$^5$ .................... G01N 27/26; G01N 27/447
[52] U.S. Cl. ................. 204/180.1; 204/299 R
[58] Field of Search ............ 204/180.1, 182.8, 299 R

[56] References Cited

U.S. PATENT DOCUMENTS

| | | | |
|---|---|---|---|
| 4,070,284 | 1/1978 | Fujita et al. | 210/31 |
| 4,805,441 | 2/1989 | Sides et al. | 73/23.25 |
| 4,908,116 | 3/1990 | Zare et al. | 204/299 |
| 4,941,958 | 7/1990 | Byers | 204/183.3 |
| 5,045,172 | 9/1991 | Guzman | 204/299 |
| 5,085,756 | 2/1992 | Swedberg | 204/299 R |
| 5,089,099 | 2/1992 | Chien et al. | 204/299 R |
| 5,116,471 | 5/1992 | Chien et al. | 204/180.1 |
| 5,202,010 | 4/1993 | Guzman | 204/180.1 X |

FOREIGN PATENT DOCUMENTS

| | | |
|---|---|---|
| 0284394 | 9/1988 | European Pat. Off. . |
| 89/04966 | 1/1989 | PCT Int'l Appl. ......... G01N 35/00 |

OTHER PUBLICATIONS

Ruedi Aebersold and Hamish D. Morrison, "Analysis of dilute peptide sample by capillary zone electrophoresis" Journal of Chromatography 516 (1990) 79-88.

Dean S. Burgi and Ring-Ling Chien, "Optimization in Sample Stacking for High-Performance Capillary Electrophoresis" Analytical Chemistry vol. 63, No. 16 (Sep. 15, 1991) 2042-2047.

Patent Abstracts of Japan-vol. 012309 (P-748) Aug. 23, 1988 and JP63079071 (Agency of Ind. Science & Technol).

Takigiku, R. et al; "Capillary-Zone Electrophoresis with Fraction Collection for Desorption Mass Spectrometry"; Rapid Communications in Mass Spectrometry, vol. 4, No. 1, 1990, pp. 24-29.

Front page of Supplemental Amendment filed on Jun. 27, 1990 in the file wrapper of U.S. Patent No. 5,045,172 (Serial No. 07/270,788).

Huang, X. et al; "Use of an On-Column Frit in Capillary Zone Electrophoresis Sample Collection"; Anal. Chem. 1990, 62, pp. 443-446.

Wallingford, R. et al; "Capillary Zone Electrophoresis with Electrochemical Detection"; Anal. Chem. 1987, 59, pp. 1762-1766.

McFadyen, Peter; "Electrophoretic Mobility and Zeta Potential of Colloidal Particles"; International Laboratory (Sep. 1986) pp. 32-42.

Terabe, Shigeru et al; Electrokinetic Chromatography With Micellar Solution and Open-Tabular Capillary; Anal. Chem. (1985) 57, pp. 834-841.

*Primary Examiner*—John Niebling
*Assistant Examiner*—John S. Starsiak, Jr.
*Attorney, Agent, or Firm*—William H. May; P. R. Harder; Wen Liu

[57] ABSTRACT

A electrophoresis column having on-column means and a method for concentrating analytes of interest in a sample prior to electrophoresis. The column comprises a section having the concentrating means upstream of a capillary section. A sample is flowed past the concentrating means which immobilizes the analytes of interest thereby concentrating the analytes of interest in the section. Thereafter the analytes are released from the concentrating means for carrying out electrophoresis.

21 Claims, 1 Drawing Sheet

ON-COLUMN PRECONCENTRATION OF SAMPLES IN CAPILLARY ELECTROPHORESIS

BACKGROUND OF THE INVENTION

1. Field of the Invention

The present relates invention relates to capillary electrophoresis and more particularly to sample preparation for electrophoresis.

2. Description of Related Art

Capillary electrophoresis is a high resolution, high sensitivity method for preparation and detection of organic analytes in mixtures. Typically, the sample mixture is introduced into one end of a capillary tube filled with buffer solution, polyacrylamide gel, or other types of separation support medium. A high voltage potential is applied across the ends of the capillary tube to cause separation of the sample mixture into various species of analytes. Analytes of the same species are resolved into bands as separation takes place. A detector detects the presence of the bands.

One of the limitations of prior art capillary electrophoresis processes is the extremely small amount of sample which can be used without degrading the resolution of the separated bands. When a large amount of sample is used, the bands are broader and the spacings between bands are narrower. Portions of adjacent bands may overlap. It would be difficult for the detector to resolve two overlapped bands. Thus, the volume of sample used is typically in the order of several nanoliters. However, when a small volume of sample is employed, and the analytes of interest are present in low concentration in the small volume, the volumes of the analytes of interest are so small that it represents a major limitation on the detectability of the analytes.

SUMMARY OF THE INVENTION

The present invention is directed to the preparation of a sample four electrophoresis by selectively raising the concentration of the species of analytes of interest prior to performing electrophoresis. This is done on-line with respect to the capillary tube. At the inlet end of the capillary tube, there is a short section which contains an active material which will selectively retain in a localized region the analytes of interest from a flow of sample. The analytes accumulated on the material are thereafter released from the material to begin electrophoresis. Effectively, a higher concentration of the species of analytes of interest is present in the remaining sample which is subject to electrophoresis.

DESCRIPTION OF THE ILLUSTRATED EMBODIMENT

The following description is of the best presently contemplated mode of carrying out the invention. This description is made for the purpose of illustrating the general principles of the invention and should not be taken in a limiting sense. The scope of the invention is best determined by reference to the appended claims.

Figure 1:
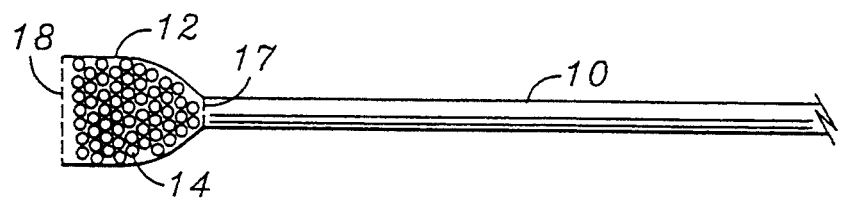
Figure 2:
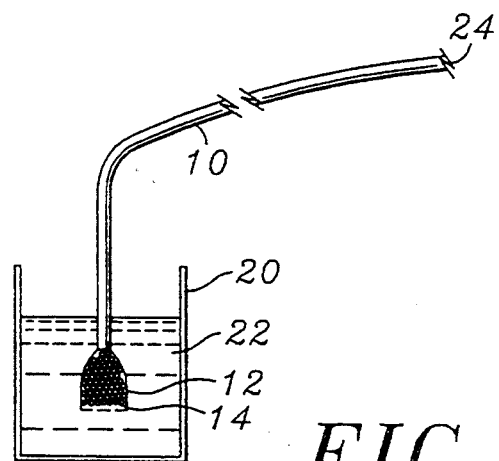
Figure 3:
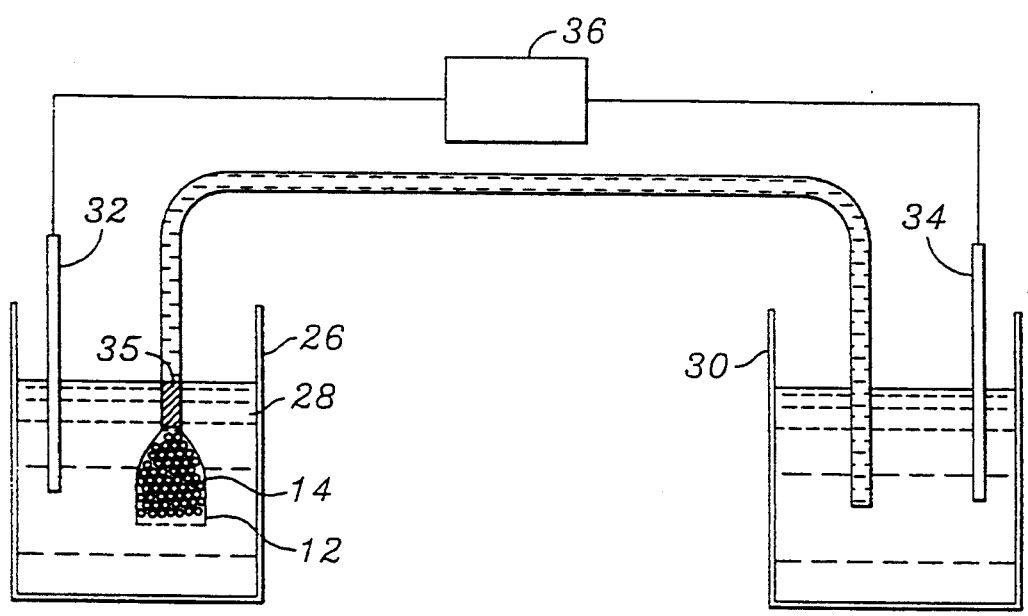

Referring to FIG. 1, the modification of a capillary tube for concentration of analytes is shown in accordance with one embodiment of the present invention. At the inlet end of the capillary tube 10, there is a section 12 which contains an active material 14 which will selectively immobilize or retain the analytes of interest in the section 12 when a sample solution containing the analytes flows past the material 14. The analytes of interest are accumulated or trapped at this section while the rest of the sample flows downstream of the capillary tube 10. The material 14 is chosen of the type that retains the species of analytes of interest by one of a number of possible mechanisms, e.g. adsorption, partition, ion exchange, antibody/antigen, or other reversible linkage mechanisms. For example, ion exchange resin can be used to immobolize proteins. The material 14 may be in particle form suitably held in the section 12 as by using porous structures 17 and 18. The section 12 may be a part of the capillary tube 10, or a separate structure coupled to the capillary tube 10. Depending on the application, the section 12 may be larger than or the same size as the inner diameter of the capillary tube 10. It may be advantageous that the section 12 have a larger inner diameter than that of the capillary tube 10 if it contains a particulate material. Specifically, the inner diameter of the section 12 is chosen such that the effective flow cross-sectional area is roughly constant throughout the section 12 and the capillary tube 10 thereby maintaining a constant flow velocity throughout the structure.

LOADING

To carry out electrophoresis, the section 12 of the capillary tube 10 is first filled with buffer and immersed in a container 20 of sample solution 22. The sample solution 22 is injected into the section 12 by pressurizing the sample container 20 or by suction at the open-end 24 of the capillary tube 10. A relatively large volume of sample solution 22 can be introduced, whereupon the analytes of interest would be retained by the material 14 in the section 12. Since back pressure will be variable, it will be necessary to optimize loading time for a particular material 14. In order to maintain a uniform electric field during electrophoresis, it is important to remove non-adsorbed sample from the system. This is accomplished with a low concentration buffer solution to wash the residual sample solution out of the capillary tube 10 prior to mobilizing the analytes. This wash buffer solution should not have the ability to remove the analytes 35 of interest from the material. In addition, in order to maintain plug flow and high resolution it will be necessary to back wash the column up to the section 12 with run buffer prior to initiating mobilization and separation.

MOBILIZATION

When sufficient analytes have accumulated in the section 12, the sample container 20 is replaced by a container 26 of buffer solution 28. The end 24 of the capillary tube 10 is immersed in another container 30 of buffer solution. Electrodes 32 and 34 are placed in the buffer solution containers 26 and 30. A high voltage source 36 is used to apply a voltage potential across the electrodes 32 and 34. The analytes 35 accumulated on the material 14 would be released by the application of low pressure and/or voltage. Alternatively, the electroosmotic flow generated in the system, and/or a change in pH or other chemical property of the buffer solution 28 may also release the analytes on the material 14. Any one of these mechanisms may be relied upon to reverse the analyte immobilization mechanism of the material 14. The section 12 may be separated from the tube 10 after the analytes 35 have been released from the material 14. The released analytes 35 undergo electrophoresis under the applied voltage.

RESOLUTION

Since a lesser number of analytes 35 are present in the remaining sample that undergo electrophoresis, there are less separated bands. It follows that it is less likely to result in overlap of adjacent bands. Thus, it can be appreciated that the process according to the present invention can be carried out starting with a large volume of sample solution without degrading the resolution of the results. The ability to work with a large volume of sample solution is advantageous in several respects. For example, the handling of small volumes is undesirable since it involves delicate procedures which are vulnerable to losses and contamination. The ability to perform on-line (with respect to the capillary tube) preconcentration of the components of interest also has several advantages. Notably, a significant advantage is that the small volume of concentrated sample components can be transferred directly to the capillary tube for electrophoretic separation without being handled by a separate transfer means, which would otherwise subject the small volumes to losses and contaminations.

While the invention has been described with respect to the preferred embodiments in accordance therewith, it will be apparent to those skilled in the art that various modifications and improvements may be made without departing from the scope and spirit of the invention. Accordingly, it is to be understood that the invention is not to be limited by the specific illustrated embodiments but only by the scope of the appended claims.

We claim:

1. An electrophoresis column for carrying out capillary electrophoresis in an electrophoresis apparatus, said column flow communicating with a buffer solution provided in the apparatus, the column comprising:
   a first section defining a capillary region for electrophoretic separation; and
   a second section defining a region upstream of the first section having means for concentrating analytes of interest in a sample carried in a buffer solution; said concentrating means includes a particulate material for releasibly immobilizing the analytes of interest which, upon subsequent release, are to be electrophoretically separated in the first section.

2. A column as in claim 1 wherein the means for concentrating comprises means for accumulating the analytes of interest in the second section as the sample flows past the second section.

3. A column as in claim 2 wherein the means for accumulating comprises an active material which will selectively immobilize the analytes of interest in the second section by reversible linkage with the analytes so that the analytes can be mobilized from the material at a later time.

4. A column as in claim 3 wherein the active material possesses reversible linkage capability by one of adsorption, partition, ion exchange or antibody-antigen mechanisms.

5. A column as in claim 4 wherein the second section is coupled to the first section.

6. A column as in claim 4 wherein the second section is integral to the first section.

7. A column as in claim 1 wherein the first section has a first inner diameter, the second section has a second inner diameter, wherein the second inner diameter is larger than the first inner diameter such that the flow cross-sectional area in the second section is substantially the same as that of the first section.

8. A capillary electrophoresis device comprising:
   a separation column having means for concentrating analytes of interest in a sample; said concentrating means includes means for releasibly immobilizing the analytes of interest which, upon subsequent release, are to be electrophoretically separated;
   means for introducing the sample into the separation column for said analytes of interest to be concentrated by the means for concentrating prior to electrophoresis in the separation column; and
   means for effecting electrophoresis of the concentrated analytes of interest in the sample in the separation column.

9. A device as in claim 8 wherein the separation column comprises:
   a first section defining a capillary region for electrophoretic separation; and
   a second section defining a region upstream of the first section having the means for concentrating.

10. A device as in claim 9 further comprising means for applying a voltage across the first section to cause electrophoretic separation of the concentrated analytes.

11. A device as in claim 9 wherein the means for concentrating comprises means for accumulating the analytes of interest in the second section as the sample flow past the second section thereby concentrating the analytes of interest.

12. A device as in claim 11 further comprising means for releasing the analytes of interest from the second section.

13. A device as in claim 11 wherein the means for accumulating comprises an active material which will selectively immobilize the analytes of interest in the second section by reversible linkage with the analytes so that the analytes can be mobilized from the material at a later time.

14. A device as in claim 13 wherein the active material possesses reversible linkage capability by one of adsorption, partition, ion exchange or antibody-antigen mechanisms.

15. A device as in claim 14 wherein the second section is coupled to the first section.

16. A device as in claim 14 wherein the second section is integral to the first section.

17. A device as in claim 14 wherein the material is in particulate form.

18. A device as in claim 14 wherein the first section has a first inner diameter, the second section has a second inner diameter, wherein the second inner diameter is larger than the first inner diameter such that the flow cross-sectional area in the second section is substantially the same as that of the first section.

19. A method of preparing a sample for electrophoresis in a capillary column comprising the steps of:
   providing on-column means for concentrating analytes of interest in a sample prior to electrophoresis in the capillary column;
   passing the sample carried in a buffer solution through the on-column means; and
   releasibly immobilizing the analytes of interest with the on-column means as the sample flows by, thereby concentrating the analytes of interest in the on-column means prior to releasing the immobilized analytes of interest to be electrophoretically separated.

20. A method as in claim 19 wherein the on-column means comprises means for immobilizing the analytes of interest as the sample flow past the on-column means.

21. A method of capillary electrophoresis comprising the steps of:
- providing a capillary column;
- providing on-column means for concentrating analytes of interest in a sample;
- passing the sample through the on-column means;
- immobilizing the analytes of interest with the on-column means as the sample flows by, thereby concentrating the analytes of interest in the on-column means;
- mobilizing the concentrated analytes of interest with respect to the on-column means; and
- performing electrophoresis on the mobilized analytes in the capillary column.

* * * * *